(12) United States Patent
Griffiths et al.

(10) Patent No.: US 7,300,644 B2
(45) Date of Patent: Nov. 27, 2007

(54) TARGETED COMBINATION IMMUNOTHERAPY

(75) Inventors: Gary L. Griffiths, Morristown, NJ (US); Hans J. Hansen, Slidell, LA (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 225 days.

(21) Appl. No.: 10/361,026

(22) Filed: Feb. 10, 2003

(65) Prior Publication Data

US 2003/0232011 A1 Dec. 18, 2003

Related U.S. Application Data

(63) Continuation of application No. 09/597,580, filed on Jun. 20, 2000, now Pat. No. 7,011,812, which is a continuation-in-part of application No. 09/184,950, filed on Nov. 3, 1998, now Pat. No. 6,077,499.

(60) Provisional application No. 60/017,011, filed on May 3, 1996.

(51) Int. Cl.
*A61K 51/00* (2006.01)
*A61M 36/14* (2006.01)

(52) U.S. Cl. .................... 424/1.49; 424/1.11; 424/9.1; 424/1.65

(58) Field of Classification Search ............... 424/1.11, 424/1.49, 1.53, 1.65, 9.1, 9.2, 9.3, 9.4, 9.5, 424/9.6, 9.7, 9.8, 1.37, 1.69; 534/7, 10–16; 514/1
See application file for complete search history.

(56) References Cited

U.S. PATENT DOCUMENTS

| | | | |
|---|---|---|---|
| 3,927,193 A | 12/1975 | Hansen et al. | |
| 4,331,647 A | 5/1982 | Goldenberg | |
| 4,348,376 A | 9/1982 | Goldenberg | |
| 4,361,544 A | 11/1982 | Goldenberg | |
| 4,444,744 A | 4/1984 | Goldenberg | |
| 4,468,457 A | 8/1984 | Goldenberg et al. | |
| 4,474,893 A | 10/1984 | Reading | |
| 4,479,895 A | 10/1984 | Auditore-Hargreaves | |
| 4,624,846 A | 11/1986 | Goldenberg | |
| 4,818,709 A | 4/1989 | Primus et al. | |
| 5,256,395 A | 10/1993 | Barbet et al. | |
| 5,283,342 A | 2/1994 | Gustavson et al. | |
| 5,420,105 A | 5/1995 | Gustavson | |
| 5,474,772 A | 12/1995 | Maddock | |
| 5,482,698 A | 1/1996 | Griffiths | |
| 5,525,338 A | 6/1996 | Goldenberg | |
| 5,736,119 A | 4/1998 | Goldenberg et al. | |
| 5,846,741 A | 12/1998 | Griffiths et al. | |
| 6,077,499 A | 6/2000 | Griffiths et al. | |
| 7,011,812 B1 * | 3/2006 | Griffiths et al. ............ 424/1.49 |
| 2003/0198595 A1 * | 10/2003 | Goldenberg et al. ....... 424/1.49 |

FOREIGN PATENT DOCUMENTS

| | | |
|---|---|---|
| EP | 0 496 074 | 7/1992 |
| JP | 3-503898 | 8/1991 |
| JP | 5501543 T | 3/1993 |
| WO | WO 94/23759 | 10/1994 |
| WO | WO 97/41898 | 11/1997 |

OTHER PUBLICATIONS

Golub et al, Science, Oct. 15, 1999, vol. 286, pp. 531-537.*
Barbet, J., et al., "Radioimmunodetection of Medullary thyroid Carcinoma Using Indium-111 Bivalent Hapten and Anti-CEA X Anti-DTPA-Indium Bispecific Antibody," The Journal of Nuclear Medicine, vol. 39, No. 7, Jul. 1998, pp. 1172-1178.
Janevik-Ivanovska, E., et al., "Bivalent Hapten-Bearing Peptides Designed for Iodine-131 Pretargeted Radioimmunotherapy" Bioconjugate Chem. 1997, 8, 526-533.
Schuhmacher, Jochen, et al., "Pretargeting of human mammary carcinoma xenografts with bispecific anti-MUC1/ anti-Ga chelate antibodies and immunoscintigraphy with PET" Nuclear Medicine and Biology 28 (2001) 821-828.
Gautherot, Emmunuel, et al., "Immunohistology of Carcinoembryonic Antigen (CEA)-expressing Tumors Grafted in Nude Mice after Radioimmunotherapy with 131I-labeled Bivalent Hapten and Anti-CEZ x Antihapten Bispecific Antibody," Clinical Cancer Research vol. 5, 3177s-3182s, Oct. 1999 (Suppl.).
Karacay, H., "Experimental Pretargeting Studies of Cancer with a Humanized anti-CEA x Murine anti-[In-DTPA] Bispecific Antibody Construct and a 99mTc-/188Re-Labeled Peptide" Bioconjugate Chem. 2000, 11, 842-854.

* cited by examiner

*Primary Examiner*—Dameron L. Jones
(74) *Attorney, Agent, or Firm*—Faegre & Benson, LLP; Richard A. Nakashima

(57) ABSTRACT

The present invention is directed to methods for treating cancer wherein more than one therapeutic agent is used, with each of the therapeutic agents having different tumor-killing capabilities, and wherein the therapeutic agents are delivered to the tumor sites using combined targeting and pretargeting methods. The methods of the present invention achieve good tumor to non-tumor ratios of the therapeutic agents, and are effective for cancer therapy.

11 Claims, 2 Drawing Sheets

TARGETED COMBINATION IMMUNOTHERAPY

BACKGROUND OF THE INVENTION

1. Field of the Invention

The present invention is directed to methods for treating cancer or an infectious disease wherein more than one therapeutic agent is used, with each of the therapeutic agents having different tumor-killing or infectious cell-killing capabilities, and wherein the therapeutic agents are delivered to the tumor sites or diseased sites using combined targeting and pre-targeting methods. The methods of the present invention achieve good tumor/disease site to non-tumor/non-disease site ratios of the therapeutic agents, and are effective for therapy.

2. Description of Related Art

Target-directed therapy, such as antibody-directed therapy, offers advantages over non-targeted therapy such as systemic therapy via oral or i.v. administration of drugs or whole body therapy such as external radiation therapy (XRT). An advantage of antibody-directed therapy, and of therapy using monoclonal antibodies (MAbs) in particular, is the ability to deliver increased doses of a therapeutic agent to a tumor, with greater sparing of normal tissue from the effects of the therapeutic agent. This directed therapy might include the use of naked MAbs or MAbs conjugated to drugs, bacterial or other toxins, radionuclides, or neutron-capturing agents, such as boron addends.

However, antibody-directed therapies have drawbacks, which include: (1) the inability to target all cancer cells within a tumor due to tumor antigen heterogeneity especially when using non-isotopic therapeutics; (2) low absolute accretion of antibody in the tumor; and (3) the use of therapeutic conjugates which cause unacceptable normal organ toxicity. The prior art treatment methods have not provided complete solutions to each of these problems.

Methods of increasing the amount of isotope which can be specifically directed to a tumor while at the same time minimizing the amount of time an isotope remains in circulation so that host toxicity is reduced are described in U.S. Pat. Nos. 5,482,698 and 5,525,338, the contents of which are incorporated by reference herein in their entirety. For example, host toxicity may be minimized by using pre-targeting techniques that decouple the isotope delivery step from the antibody localization step. In addition, these patents disclose methods for amplifying the amounts of therapeutic agents which may be delivered to tumor sites. These methods also are useful in accordance with the present invention. U.S. Pat. No. 4,624,846, discloses methods for reducing host toxicity by administering a second antibody to clear circulating radiolabeled first antibody. Co-pending U.S. application Ser. No. 08/486,166, filed Jun. 7, 1995, the contents of which are incorporated by reference herein in their entirety, teaches the use of an antibody that is anti-idiotypic to the first administered (radiolabeled) primary targeting species as a clearing agent in pre-targeting methods. These methods also may be used in accordance with the present invention, and the contents of the aforementioned patents are incorporated herein by reference in their entirety.

Although these patents and patent applications disclose methods which address several of the problems associated with target-directed therapies, none of them address the problem caused by tumor antigen heterogeneity. Additionally, there is a continuing need to utilize the specificity of a targeting moiety to simultaneously deliver tumor-killing amounts of therapeutic agents to tumors yet sparing the toxic effect of these agents on normal tissues. The present invention provides a solution to these problems by disclosing a method that utilizes multiple targeting and pre-targeting administrations to deliver more than one therapeutic agent to the tumor. Preferably the therapeutic agents have different tumor killing properties so that. more cells in the tumor can be targeted and killed. Further, the present methods maximize and amplify the mole amounts of therapeutic agents delivered per mole of antibody to address the low absolute target accretion levels of antibody. To solve the problem of low antibody-to-normal tissue ratios, at least one therapeutic agent is delivered in a later treatment step.

SUMMARY OF THE INVENTION

The present invention provides a method for therapy to tumors and infectious diseases, including bacterial, viral and fungal diseases. It comprises administering a first conjugate, which contains a targeting moiety, a therapeutic agent, and a first member of a binding pair; then optionally administering a clearing agent to clear non-targeted first conjugates; and then administering a second conjugate, which contains the complementary binding member of the binding pair and a second therapeutic agent.

The method of the present invention delivers more than one therapeutic agent to a tumor or diseased site using both targeting and pre-targeting methods to achieve effective and efficient delivery of the agents to the sites. The present invention provides a therapy method that addresses the problem of tumor heterogeneity by using multispecific targeting agents and by delivering at least two different therapeutic agents having different tumor-killing properties to the tumor sites.

The present invention further provides a therapy method that minimizes patient toxicity caused by the therapeutic agents by using pre-targeting and targeting methods of delivery.

The present invention additionally provides a therapy method with reduced toxic effects on normal tissue by utilizing clearing agents in combination with the targeting and pre-targeting methods of delivering more than one therapeutic agent to efficiently clear non-localized targeting moieties from circulation.

DETAILED DESCRIPTION

Figure 1:
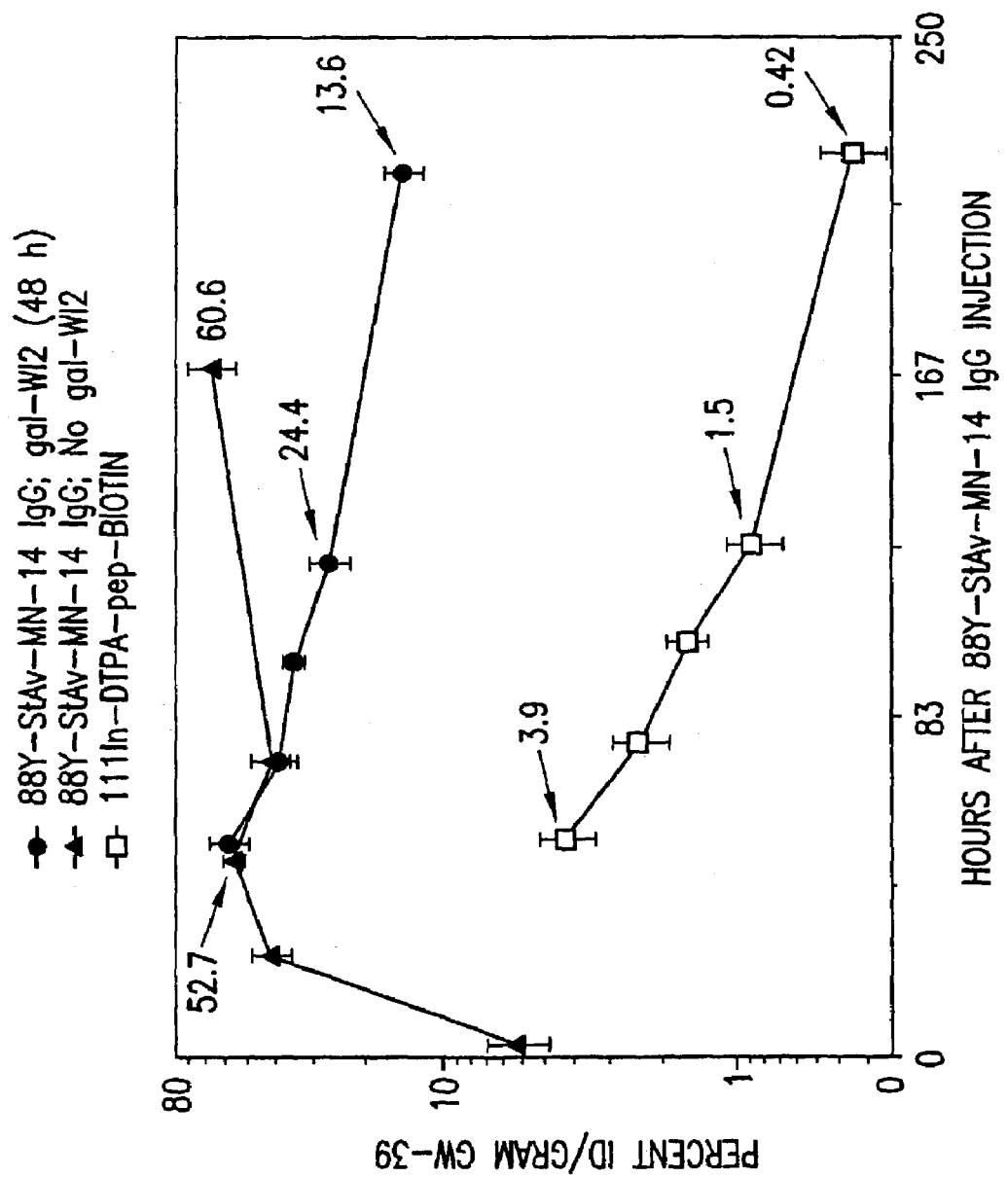
FIG. 1 shows the percentage ID/g of Y-88-DTPA-MN14 (anti-CEA)-streptavidin conjugate with and without clearing anti-idiotypic antibody to MN14, WI2; and 111-In-DTPA-pep-Biotin in tumors at continuing time points.

The present method of therapy specifically includes the following steps:

(A) administering to the patient a first conjugate comprising a targeting moiety, a first member of a binding pair, and a first therapeutic agent, where the targeting moiety selectively binds to a marker substance produced by or associated with said tumor or with an infectious disease causing agent, and allowing the first conjugate to localize at the tumor or disease site, thereby effecting therapy on the tumor or diseased tissue;

(B) optionally, administering to the patient a clearing composition, and allowing the clearing composition to clear non-localized first conjugate from circulation;

(C) administering to the patient a second conjugate comprising a complementary member of the binding pair and a second therapeutic. agent, where the second therapeutic agent is the same as or different from the first therapeutic agent, and allowing the second conjugate to localize at the tumor or disease site, thereby effecting therapy of the tumor or diseased tissue.

The targeting moiety is an antibody or an antigen binding antibody fragment capable of specifically binding to at least one epitope on the marker substances associated with, produced by or on the surface of the tumor or infectious disease causing agent, or on a component of the second conjugate. The antibody or antibody fragment may be monospecific or multispecific. Both polyclonal and monoclonal antibodies may be used, as well as certain recombinant antibodies, such as chimeric and humanized antibodies and fusion proteins. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain. Human antibodies are antibodies that either are isolated from humans and then grown out in culture or are made using animals whose immune systems have been altered so that they respond to antigen stimulation by producing human antibodies. Other techniques for making human antibodies are well known to those of skill in the art, such as in vitro phage display. A fusion protein is a recombinantly produced antigen-binding molecule in which two or more different single-chain antibody or antibody fragment segments with the same or different specificities are linked. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

The targeting moiety may be multivalent and/or multispecific. By "multivalent" it is meant that the subject targeting moiety may bind more than one target, which may have the same or a different structure, simultaneously. By "multispecific" it is meant that the subject agents may bind simultaneously to at least two targets which are of different structure. For example, a targeting moiety having two. different specificities would be considered multivalent and multispecific because it can bind two structurally different targets simultaneously. On the other hand, a molecule which having two or more specific arms which bind the same target, but no other specificities, would be multivalent but not multispecific.

Some preferred targeting moieties are bispecific, but in some cases additional specificities, e.g. two to six, are preferred. Similarly, some preferred targeting moieties are bivalent, but increasing the valency of the agent would be beneficial in binding either additional molecules of the same target or multiple different targets.

The targeting moiety can also be a non-antibody species selecting from the group consisting of proteins, peptides, polypeptides, enzymes, and oligonucleotides.

The primary targeting species carrying the first therapy agent, for instance, a radiolabeled bispecific antibody, can be raised against a specific second therapy agent, or against a conjugate comprising a therapy agent and a recognition moiety. In the first embodiment, one can, for example, use a radiolabeled bispecific antibody targeted dually against CEA and the camptothecin ring system. In this instance, the second step agent, is then used to deliver standard chemotherapy, such as one of the camptothecin-based anticancer compounds, such as CPT-11 (Irinotecan), topotecan or 10-hydroxycamptothecin.

Preferred targeting moieties bind different antigens or different epitopes of the same antigen on a targeted cell. In a further preferred embodiment, a targeting moiety is used that comprises an arm that is specific for a low-molecular weight hapten to which a therapeutic agent is conjugated or fused. In this case, the antibody pretargets the cells, and the low-molecular weight hapten with the attached therapeutic agent is administered after the antibody has bound to the targets. Examples of recognizable haptens include, but are not limited to, chelators, such as DTPA, fluorescein isothiocyanate, vitamin B-12 and other moieties to which specific antibodies can be raised. The subsequently injected haptens can carry different therapeutic agents. More than one multispecific antibody also may be used, each of which comprises an arm which recognizes the same hapten. The use of multispecific antibodies, and combinations of multispecific antibodies, provides an effective technique for overcoming antigen heterogeneity in tumors and other diseased tissue, and also enhance binding of a second reagent (hapten/drug or isotope) to the target.

The use of hapten-therapy agent conjugates for the localization of therapeutics to disease targets has several distinct advantages. The same hapten can be attached to several different therapy agents. In addition, should an immune response to one therapy agent be seen, this will not destroy the ability of a developed non-immunogenic antibody targeting vector to be used in hapten-therapy agent-based systems. This also enables the use of a universal targeting system that can be used with any targeting antibody and therapy agent combination. In using a hapten recognition system the designing chemist has control over how haptens are attached to a therapy agent, and is able to incorporate features such as lability to a particular extra-cellular or intracellular enzyme, or instability to a particular set of conditions, such as slightly lowered pH.

The binding pair is selected from the group consisting of avidin or streptavidin and biotin, complementary DNA fragments, complementary peptide oligonucleotides, enzymes and their corresponding prodrug substrates and multispecific antibody or antibody fragment and corresponding hapten. The first member of the binding pair preferably is a multispecific, preferably bispecific, antibody or antibody fragment that includes a specificity for a low molecular weight hapten. The second member of the binding pair is the complementary hapten. More specifically, the method employs a first conjugate comprises one arm that selectively binds to the marker substance, a second arm that binds to a marker substance, and a therapeutic agent. The second conjugate is a hapten which carries a second therapeutic agent, which may be the same or different from the first therapeutic agent. Both of the conjugates may comprise a radiolabel as the therapeutic agent, and where this is the case it is preferable to use two radionuclides which emit different levels of radiation. A clearing agent which binds to the first conjugate may be used, and is preferably anti-idiotypic to the targeting moiety, and more specifically an anti-idiotypic antibody. More preferably the anti-idiotypic antibody is substituted with galactose and biotin residues.

The first and second therapeutic agents are selected from the group consisting of radionuclides, drugs, toxins, and boron addends. If both therapeutic agents are radionuclides, then it is preferably that each of the radionuclides emit different levels of radiation. Suitable therapeutic radionuclides include of I-131, I-125, At-211, P-32, P-33, Sc-47, Cu-64, Cu-67, As-77, Y-90, Ph-105, Pd-109, Ag-111, I-125, Pr-143, Sm-153, Tb-161, Ho-166, Lu-177, Re-186, Re-188, Re-189, Ir-194, Au-199, Pb-212, and Bi-213. Preferably the first therapeutic agent is selected from the group consisting of I-131, I-125 and At-211, and the second therapeutic agent is selected from the group consisting of P-32, P-33, Sc-47, Cu-64, Cu-67, As-77, Y-90, Ph-105, Pd-109, Ag-111, I-125, Pr-143, Sm-153, Tb-161, Ho-166, Lu-177, Re-186, Re-188, Re-189, Ir-194, Au-199, Pb-212, and Bi-213.

Alternatively the second therapeutic agent is a boron addend, and the method further comprises irradiating the tumor with thermal or epithermal neutrons after localization of the second conjugate at the tumor. The second therapeutic agent alternatively may comprise a drug-polymer conjugate, a PEG-drug conjugate or a drug-liposome conjugate.

A preferred embodiment uses the delivery of polymeric drug conjugates in the second step therapy. Here, a bispecific antibody-therapy agent conjugate is given, wherein the secondary recognition arm recognizes some part of a polymeric therapy agent. Typically such agents would have a general formula comprising a (recognition hapten)$_n$-(polymer backbone)-(therapy moiety)$_m$, or a polymer backbone-(therapy moiety)$_m$ wherein n and m are integers reflecting different substitution levels on the polymer backbone for the respective species. Of course, linkage of a drug directly onto a polymer can result in the definition of a polymer-drug complex as a prodrug, since one expects that the drug will exert its affect after cleavage and the polymer-drug complex will inherently have a lower toxicity profile than the free drug.

Many methods exist for the attachment of various drugs to polymeric backbones. Basically, all that is needed from the chemist's point-of-view is complementary functional groups on both polymer and drug. For example, the chemotherapy agent SN-38 has a free hydroxyl group in the 10-position of its A-ring. This can be used as a reactive group with polymers containing free carboxyl groups to generate a camptothecin-containing polymer wherein the drug units are attached as phenyl ester derivatives. Built into this conjugate is the concept that the camptothecin-containing polymer has a stability profile that has a limited life span in vivo due to the relative lability of the phenyl ester linkages. The bispecific antibody-therapy agent conjugate used in the first step, can recognize, via its secondary recognition antibody arm, either the camptothecin moieties or the polymer backbone.

Varying the linkage chemistries between drug and polymer can vary the stability profile of the polymer-drug conjugate. For instance, in the same exemplary class, one can attach SN-38 to a poly-amino containing polymer [e.g. poly-lysine]. Here, the 10-hydroxycamptothecin-containing SN-38 has its 10-hydroxy group converted to an intermediate chlorocarbonyl derivative by reaction with phosgene. That reactive intermediate is used, in turn, for reaction with the poly-amine polymer to generate SN-38 units attached by urethane bonds, which are somewhat more stable than ester bonds, but are thought not as stable as, for instance, amide bonds.

In a preferred embodiment, a fully structurally defined polymeric carrier is used rather than random co-polymers such as the polylysine, polyglutamate and dextrans used in much prior polymer-drug work. For instance, a decapeptide can be easily assembled using standard peptide synthesis chemistry. Again, in the case of SN-38-containing conjugates, the peptide can have from 1-10 glutamyl [or other acid] residues. Further, if the secondary arm of the bispecific antibody-therapy agent conjugate, first given is raised against a more universal hapten, such as DTPA, several DTPA moieties can be further appended to the polymer-SN-38 conjugate, for recognition purposes.

The drug can be internalized after cleavage from the polymer. Or, it can be internalized as part of an intact complex, by virtue of cross-linking of the primary targeting bispecific antibody-therapy agent at the target. The (recognition hapten)$_n$-(polymer backbone)-(prodrug therapy moiety)$_m$ may induce internalization of tumor-bound bsmab as the entire complex and such an internalization aspect of bsmab delivered drug conjugates can be important for improved efficacy. Since the internalization properties of antibodies constitute a continuum, in the sense that all mabs are internalized to some extent. Theory suggests that a 'non-internalizing' mab be used for a binary delivery system. However, particularly for a drug, or dual-drug approach, a relatively high rate of internalization in a prodrug may be preferred. Within the binary delivery nature of the bispecific system, the lower availability of drug-hapten binding sites may be somewhat offset by the increased efficacy due to higher levels of internalized drug. Particularly, if internalization is triggered or enhanced after cross-linking of first-targeted bispecific antibody-therapy agent by drug-bearing conjugates recognized by the pretargeted bispecific.

Any [drug-polymer-recognition hapten] conjugate can be employed in the invention. Preferred combinations will include agents chosen for convenience of chemical preparation. In coupling the species together, main chemical bond forming reactions will include, but not be limited to, the formation of amides, esters, carbamates, ureides, and thio derivatives of the same. Exemplary polymeric carriers of the invention are polyamino acids such as polylysine, polyglutamic (E) and aspartic acids (D), including D-amino acid analogs of the same. Co-polymers such as poly(Lys-Glu) {poly[KE]} desirable ratios to each other, advantageously from 1:10 to 10:1, may be used. Copolymers based on amino acid mixtures such as poly(Lys-Ala-Glu-Tyr) (KAEY; 5:6:2:1) may also be employed.

Smaller polymeric carriers of defined molecular weight can be produced by solid-phase peptide synthesis techniques, readily producing polypeptides of from 2-50 residues chain length. A second advantage of this type of reagent, other than precise structural definition, is the ability to place single or any desired number of chemical handles at certain points in the chain. These can be later used for attachment of recognition and therapeutic haptens at chosen levels of each moiety.

Poly(ethylene) glycol [PEG] has desirable in vivo properties for use in this approach. Ester linkages between the hydroxyl group of SN-38 and both ends of a standard di-hydroxyl PEG can be introduced by insertion of diacids such as succinic acid between the SN-38 and PEG hydroxyl groups, to generate species such as SN-38-O—CO(CH2)$_2$CO—O-PEG-O—CO(CH2)$_2$CO—OSN-38. The di-SN-38-

PEG produced can be considered as the shortest member of the class of SN-38-polymer prodrugs. The desirable in vivo properties of PEG derivatives and the limited loading capacity due to their dimeric functionality led to the preparation of PEG co-polymers having greater hapten-bearing capacity such as those described by Poiani et al. (Bioconjugate Chem., 5:621-630, 1994). PEG derivatives activated at both ends as their bis(succinimidyl)carbonate derivatives and co-polymerized with multi-functional diamines such as lysine. The product of such co-polymerization, containing (-Lys(COOH)-PEG-Lys(COOH)-PEG-)$_n$ repeat units wherein the lysyl carboxyl group is not involved in the polymerization process, can be used for attachment of SN-38 residues. The SN-38 residues are reacted with the free carboxyl groups to produce SN-38 esters of the (-Lys (COOH)-PEG-Lys(COOH)-PEG-)$_n$ chain.

Other synthetic polymers that can be used to carry recognition and drug haptens include N-(2-hydroxypropyl) methacrylamide (HMPA) copolymers, poly(styrene-co-maleic acid/anhydride) (SMA), poly(divinylether maleic anhydride) (DIVEMA), polyethyleneimine, ethoxylated polyethyleneimine, starburst dendrimers and poly(N-vinylpyrrolidone) (PVP). As an example, DIVEMA polymer comprised of multiple anhydride units is reacted with a limited amount of SN-38 to produce a desired substitution ratio of drug on the polymer backbone. Remaining anhydride groups are opened under aqueous conditions to produce free carboxylate groups. A limited number of the free carboxylate groups are activated using standard water-soluble peptide coupling agents (e.g. EDAC) and coupled to a recognition moiety bearing a free amino group. An example of the latter would be histamine, to which antibodies have been raised in the past.

The above exemplifications of polymer use are directed toward SN-38, the active metabolite of the prodrug CPT-11 (irinotecan), as an example. SN-38 has an aromatic hydroxyl group that was used in the above descriptions to produce aryl esters susceptible to esterase-type enzymes. Similarly the camptothecin analog topotecan, widely used in chemotherapy, has an available aromatic hydroxyl residue that can be used in a similar manner as described for SN-38, producing esterase-susceptible polymer-prodrugs.

Doxorubicin and other drugs with amino 'chemical handles' active enough for chemical coupling to polymeric carriers can be effectively coupled to carrier molecules via these free amino groups in a number of ways. Polymers bearing free carboxylate groups can be activated in situ (EDAC) and the activated polymers mixed with doxorubicin to directly attach the drug to the side-chains of the polymer via amide bonds. Amino-containing drugs can also be coupled to amino-pendant polymers by mixing a commercially available, and cleavable cross-linking agent such as ethylene glycobis(succinimidylsuccinate) (EGS, Pierce Chemical Co., Rockford, Ill.) or bis-[2-(succinimidoxycarbonyloxy)ethyl]sulfone (BSOCOES, Molecular Biosciences, Huntsville, Ala.) to cross-link the two amines as two amides after reaction with the bis(succinimidyl) ester groups.

Methotrexate also has an available amino group for coupling to activated carboxylate-containing polymers, in a similar manner to that described for doxorubicin, above. It also has two glutamyl carboxyl groups (alpha and gamma) that can be activated for coupling to amino-group containing polymers. The free carboxylate groups of methotrexate can be activated in situ (EDAC) and the activated drug mixed with an amino-containing polymer to directly attach the drug to the side-chains of the polymer via amide bonds. Excess unreacted or cross-reacted drug is separated readily from the polymer-drug conjugate using size-exclusion or ion exchange chromatography.

Maytansinoids and calicheamicins (such as esperamycin) contain mixed di- and tri-sulfide bonds that can be cleaved to generate species with a single thiol useful for chemical manipulation. The thiomaytansinoid or thioesperamycin can be reacted with a maleimido- or thiol-containing polymer, effecting linkage of the drugs via thioether or disulfide bonds.

When the drug itself, or the polymer backbone is not used as the recognition unit, a separate hapten can also be attached to the polymer, preferably a hapten useful for universal recognition when attached to any polymer-drug conjugate. When recognition haptens are briefly discussed above, the chelate diethylenetriaminepentaacetic acid (DTPA) is the recognition hapten used in much of that discussion. Antibodies have been raised against indium-DTPA by at least two independent laboratories. Antibodies can be reactive against the free chelate or a metal complex of the chelate. Antibodies can and do have different affinities for DTPA when the chelate is complexed with different metals. This can be used to advantage since the anti-recognition hapten arm of a bispecific antibody can be tailored for affinity by simply varying the metal held by the chelate. It has been argued that higher affinity antibodies are not able to penetrate solid tumors as deeply or evenly as lower affinity antibodies due to stronger affinity binding at the tumor target surface cells. Antibodies have also been raised against other metal chelates, such as 1,4,7,10-tetraza-cyclododecane-N,N',N'',N'''-tetraacetic acid (DOTA), or N,N'-di[2-hydroxy-5-(ethylene-3-carboxy)benzyl]ethylenediamine N,N'-diacetic acid (HBED).

The recognition hapten of the current invention does not need to be a metal-chelate complex. Other hydrophilic low molecular weight molecules capable of generating a strong immune response can be used to prepare antibodies. An instance of this is the histamine-succinate moiety together with the 679 antibody to histamine succinate, described in the scientific literature. One can contemplate many more immunogens that could be used to raise antibodies useful under in vivo conditions. Commonly used immunogens include fluorescein, 2,4-dinitrophenyl-derivatives and biotin. The last mentioned is less preferred than the former two, since recognition haptens that are not normally present in living systems are preferred. Carboxyl-containing chelate derivatives such as DTPA, DOTA, HBED and HSG are readily coupled to amino-containing polymers by controlled activation of a limited number of their carboxylate groups using EDAC-like reagents. Fluorescein is readily coupled to amine-containing polymers using an isothiocyanate-derivatized analog.

Further, the first and second therapeutic agents are mixtures of at least two radionuclides, drugs, toxins or boron addends.

In another embodiment of the present invention, the first therapeutic agent is a radionuclide and the second therapeutic agent is a drug, a toxin, or a boron addend. As described above, the first therapeutic agent is selected from the group consisting of I-131, I-125 and At-211. The second therapeutic agent is a drug and is selected from the group consisting of taxol, nitrogen mustards, ethylenimine derivatives, alkyl sulfonates, nitrosoureas, triazenes, folic acid analogs, pyrimidine analogs, purine analogs, vinca alkaloids, antibiotics, enzymes, platinum coordination complexes, substituted urea, methyl hydrazine derivatives, adrenocortical suppressants, hormones, antagonists, camptothecin, and endostatin.

The second therapeutic agent can alternatively be a toxin is selected from the group consisting of abrin, alpha toxin, diphtheria toxin, exotoxin, gelonin, pokeweed antiviral protein, ricin, saporin, DNAse and RNAse. A preferred RNAse has the sequence of RNAse from frog oocytes.

In a further embodiment of the present invention the first therapeutic agent is a drug or toxin and the second therapeutic agent is a radionuclide or a boron addend. Examples of useful drugs, toxins, and radionuclides are described above.

The therapeutic agent also may be a cytokine, lymphokine, chemokine, or immunomodulator. In a preferred embodiment a multispecific, preferably bispecific, cytokine fusion protein is administered in a first step, followed by administration of a therapeutic radionuclide as the second step. For example, a bispecific fusion protein of hMN14, a humanized monoclonal anti-CEA antibody, h734, a humanized anti-di-DTPA antibody fragment, and a cytokine such as IL2 can be used. Accordingly to this embodiment, [hMN14-Fab]-[h734-sFv]-IL2 can be administered in a first step, followed by DTPA-peptide-radiolabeled with a therapeutic radionuclide. Alternatively, [hMN14-Fab-[h734-sFv] radiolabeled with a therapeutic radionuclide can be used as the first step, followed by DTPA-IL2.

The first conjugate may comprise an antibody which is itself therapeutic, i.e., it may be a therapeutically-effective "naked" antibody, in which case no additional therapeutic agent needs to be conjugated to it. For example, IgG1 effects ADCC and/or complement fixation. An antibody against EGF [anti-hEGF-IgG/734] will block the EGF receptor, and then a second therapeutic can be administered subsequently. An anti-CD20 monoclonal bispecific antibody also can effect ADCC, complement activation, and/or apoptosis. The second conjugate then comprises a more conventional drug, toxin, cytokine or radionuclide.

This method specifically addresses the problem of disease heterogeneity which normally presents in a clinical setting. The heterogeneity is addressed by targeting both large tumors and small micrometastases within the same therapeutic method. For example, both a high-energy (highly penetrating) beta-emitter and a low or medium energy beta-emitter which exerts its penetrating effect over much shorter distances are administered to target tumor sites. For treating a disease that is more limited, a medium-energy beta-emitter may be penetrating enough to treat the larger tumors. In this embodiment, both a medium-energy beta-emitter and a low-energy beta-emitter or, preferably, a drug or toxin are delivered to tumor sites.

Cancer sites that can be targeted and treated in accordance with the present invention include carcinomas, melanomas, sarcomas, neuroblastomas, leukemias, lymphomas, gliomas and myelomas. The method is particularly well-suited for therapy of limited metastatic disease, for example, for patients who present with multiple-site tumors, up to about 5 cm in diameter.

Tumors of up to about 5 cm in diameter are those tumors which are at the maximum effective range of the most penetrating radionuclide usable with radioimmunotherapy, the pure beta-particle-emitting yttrium-90 (Y-90) nuclide. The tumor of optimum diameter for use with this nuclide is one of 3.4 cm, and the isotope's effectiveness falls off dramatically above and below this optimum diameter, such that the optimum range for a tumor targeted with Y-90 is between 2.8 and 4.2 cm. O'Donoghue et al., *J. Nucl. Med.*, 36: 1902-1909 (1995). This isotope may be less effective against small tumor deposits, and an isotope of shorter range will also be needed for dual isotope radiation. O'Donoghue et al., supra.

A tumor of 5 cm diameter weighs approximately 65 g ($\frac{4}{3}\pi r^3$; where 1 cm$^3$=1 g weight), and contains 6.5×10$^9$ cells. An average cell may be 5-20 micron in diameter. For optimum tumor cell eradication, it appears that an isotope of one particular energy will probably fail to deliver effective toxicity to a tumor in this range. Twenty-two isotopes have been reported that could be used in the context of a doubly radiolabeled antibody. O'Donoghue et al., supra. However, for the very smallest tumor deposits, and for single cells, few of the available isotopes may be useful, and a drug or toxin may be more appropriate.

The method of the present invention comprises at least two steps. In the first step, a conjugate comprising a targeting moiety, a member of a binding pair and a first therapeutic agent is administered. After the first conjugate has been administered and allowed to localize, and, preferably, after time for maximum tumor uptake of the conjugate has passed, a second conjugate is administered. This conjugate comprises the complementary member of the binding pair used in the first step and a second therapeutic agent. This conjugate localizes at the tumor sites by way of the binding pair. For example, if a radiolabeled MAb-avidin conjugate is administered in the first step, the second conjugate comprises biotin. The binding affinity between avidin and biotin will result in the second conjugate binding to the avidin already localized at the tumor sites. As a result, the second conjugate also is localized at the tumor sites. Because each avidin moiety can bind up to four biotin moieties, amplification is achieved in this step.

Optionally, a clearing step may be performed between the two steps described above. That is, after the first conjugate has had time to localize at the tumor sites, a clearing agent may be administered to remove circulating conjugate.

Targeting Moieties

The targeting moiety may be, for example, an antibody or an antigen binding antibody fragment. Monoclonal antibodies are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies also are contemplated, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the present invention include F(ab')$_2$, F(ab)$_2$, Fab', Fab, Fv and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This will include genetically engineered and/or recombinant antibodies and proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is incorporated herein by reference.

Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin. The fragments may also be produced by genetic engineering.

It should be noted that mixtures of antibodies and immunoglobulin classes can be used, as can hybrid antibodies. Multispecific, including bispecific and hybrid, antibodies and antigen binding antibody fragments are useful in the methods of the present invention. Bispecific and hybrid antibodies are capable of specifically binding to at least one epitope on the marker substances, or on a component of the second conjugate. These antibodies preferably are comprised of at least two different substantially monospecific antibodies or antibody fragments, which specifically bind to at least one epitope on the marker substance produced by or associated with the cancer cells and with at least one epitope of a component of the second conjugate. Multispecific antibodies and antibody fragments with dual specificities can be prepared analogously to the anti-tumor marker hybrids disclosed in U.S. Pat. No. 4,361,544, the contents of which are incorporated by reference herein in their entirety. Other techniques for preparing hybrid antibodies are disclosed in, e.g., U.S. Pat. Nos. 4,474,893 and 4,479,895, and in Milstein et al., *Immunol. Today*, 5: 299 (1984), the contents of which are incorporated by reference herein in their entirety.

Preferred are antibodies having a specific immunoreactivity to a marker substance produced by or associated with the cancer cells of at least 60% and a cross-reactivity to other antigens or non-targeted substances of less than 35%. A monoclonal antibody that specifically targets tumor sites by binding to antigens produced by or associated with the tumors is particularly preferred.

Antibodies against tumor antigens are known. For example, antibodies and antibody fragments which specifically bind markers produced by or associated with tumors have been disclosed, inter alia, in Hansen et al., U.S. Pat. No. 3,927,193, and Goldenberg U.S. Pat. Nos. 4,331,647, 4,348,376, 4,361,544, 4,468,457, 4,444,744, 4,818,709 and 4,624,846, the contents of all of which are incorporated herein by reference in their entirety. In particular, antibodies against an antigen, e.g., a gastrointestinal, lung, breast, prostate, ovarian, testicular, brain or lymphatic tumor, a sarcoma or a melanoma, are advantageously used.

The antibodies and antigen binding antibody fragments useful in the methods of the present invention may conjugated to the member of the binding pair by a variety of methods known in the art to include chemical conjugation and recombinant methods for making fusion proteins. Many of these methods are disclosed in the above-referenced U.S. Patents and Patent Applications. See also Childs et al., *J. Nuc. Med.*, 26: 293 (1985), the contents of which are incorporated by reference herein in their entirety.

Some cell surface components of cancer cells are common to normal cells and others are either qualitatively distinct for or quantitatively increased in tumor cells. Cell surface components common to both normal and malignant cells include, e.g., various kinds of receptors (e.g., certain hormone receptors), histocompatibility antigens, blood group antigens, and differentiation antigens. Receptors include, e.g., sheep erythrocyte receptor, hormone receptors, e.g., estrogen receptor and the like, transferrin receptor, Fc immunoglobulin receptor, nerve growth factor receptor, and the like. Blood group antigens include, e.g., the P determinant and M and N precursor ("T antigen"). Examples of differentiation antigens include surface immunoglobulin, and onco-neural antigens. Examples of histocompatibility antigens include HLA-A, HLA-B, HLA-DR (Ia-like). In cases where the cell-surface antigen is qualitatively distinct for cancer cells or quantitatively increased in cancer as compared to non-cancer tissues such cell surface markers will be useful as targets for localizing antibodies.

Tumor-associated markers have been categorized by Herberman, "Immunodiagnosis of Cancer", in Fleisher ed., "The Clinical Biochemistry of Cancer", page 347 (American Association of Clinical Chemists, 1979), in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG), which stimulates the production of antibodies having a greatly reduced cross-reactivity to non-tumor substances. Suitable such marker substances to which specific antibodies may be raised which are useful in the present invention include, but are not limited to, alpha-fetoprotein (AFP), human chorionic gonadotropin (HCG) and/or its beta-sub-unit (HCG-beta), colon-specific antigen-p (CSAp), prostatic acid phosphatase, pancreatic oncofetal antigen, placental alkaline phosphatase, pregnancy beta$_1$-globulin, parathormone, calcitonin, tissue polypeptide antigen, T-antigen, beta$_2$-microglobulin, galactyosyl transferase-II(GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cystoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA) and tumor angiogenesis factor (TAF).

Examples of tumor-specific or tumor-associated antigens include CEA, melanoma cell surface antigens, breast cancer cell surface antigens, lung cancer cell surface antigens, colorectal cancer cell surface antigens, gastric cancer cell surface antigens, pancreatic cancer cell surface antigens, glioma cell surface antigens, common sarcoma cell surface antigens, gastrointestinal cancer cell surface antigens, brain tumor cell surface antigens, esophageal cancer cell surface antigens, common epithelial cancer cell surface antigens, osteosarcoma cell surface antigens, fibrosarcoma cell surface antigens, urinary bladder cancer cell surface antigens, prostatic cancer cell surface antigens, renal cancer cell surface antigens, ovarian cancer cell surface antigens, testicular cancer cell surface antigens, endometrial cancer cell surface antigens, cervical cancer cell surface antigens, Hodgkin's disease cell surface antigens, lymphoma cell surface antigens, leukemic cell surface antigens, trophoblastic tumor cell surface antigens, and the like.

An antibody preferred for use in the present invention is MN-14, a second generation CEA-antibody that has ten times more affinity for CEA than the first generation version, NP-4. Hansen et al., *Cancer*, 71: 3478-85 (1993). MN-14 internalizes slowly, making it suitable for a pre-targeting approach.

Other targeting moieties useful in the present invention include, for example, proteins, peptides, polypeptides, glycoproteins, lipoproteins, phospholipids, oligonucleotides, steroids, alkaloids or the like, e.g., hormones, lymphokines, growth factors, albumin, cytokines, enzymes, immune modulators, receptor proteins, antisense oligonucleotides, antibodies and antibody fragments, which preferentially bind marker substances that are produced by or associated with the target site.

Binding Pair

A common binding pair used in pre-targeting methods is avidin or streptavidin and biotin. Avidin, found in egg whites, has a very high binding affinity for biotin, which is a B-complex vitamin. Wilcheck et al., *Anal. Biochem.*, 171: 1 (1988). Streptavidin, derived from *Streptomyces avidinii*, is similar to avidin, but has lower non-specific tissue binding, and therefore often is used in place of avidin. Both avidin and streptavidin have a tetravalency for biotin, thus permitting amplification when the former bind to biotin. Modified forms of avidin, such as deglycosylated avidin, charge-neutralized avidin, or deglycosylated and charge-neutralized avidin also are useful in the invention.

As used herein, "biotin" includes biotin, commercial biotin products in which the biotin has been modified by the addition of alkyl groups, and biotin derivatives such as active esters, amines, hydrazides and thiol groups with the complementary reactive groups on polymers being amines, acyl and alkyl leaving groups, carbonyl groups and alkyl halides or Michael-type acceptors.

The streptavidin-biotin system represents the strongest non-covalent biological interaction known between a protein and a ligand ($K_a = 10^{15}$ $M^{-1}$). Rosebrough, *Nucl. Med. Biol.*, 20: 663-68 (1993). Also, streptavidin has pI of 6 compared to >10 for avidin, which renders SAv's charge close to neutral at physiological pH in contrast to avidin's strong positive charge. Moreover, avidin is 'sticky' in vivo and in vitro. Rosebrough, supra. For these reasons, streptavidin is preferred to avidin for preparing conjugates used in accordance with the present invention, and the streptavidin/biotin system is a preferred binding pair for use in the present invention. It is to be understood, however, that either avidin or streptavidin may be used in accordance with the present invention. Accordingly, as used herein, either avidin or streptavidin are intended to include both avidin and streptavidin.

Methods for conjugating biotin and avidin to therapeutic agents and/or antibodies are known, and are described, for example, in co-pending U.S. application Ser. No. 08/486, 166, the contents of which are incorporated herein by reference in their entirety.

When streptavidin (or avidin) is the first member of the binding pair, and biotin is the complementary member of the binding pair, the second conjugate (the biotin-therapeutic agent conjugate) may comprise two or more moieties of biotin. This enhances the conjugate's ability to localize at the target site and allows the biotin to cross-link the radiolabeled streptavidin-Mab conjugate pre-targeted at the target sits, inducing internalization of the second therapeutic agent into the targeted tumor cells.

Complementary DNA fragments also may be used as binding pairs. Bos et al., *Cancer Res*. 54: 3479-3486 (1994). Thus, in accordance with the present invention, the first conjugate may comprise antibody, therapeutic agent and a single-stranded oligonucleotide, and the second conjugate may comprise a complementary single-stranded oligonucleotide and a therapeutic agent. A major advantage of this system over biotin/avidin systems could be the presumed lower immunogenicity of a relatively short piece of DNA compared to the immunogenic 60,000 Dalton avidin species.

In another preferred embodiment, the first member of the binding pair is an oligonucleotide analog, such as a single-chain peptide nucleic acid, and the complementary member of the binding pair is the complementary peptide nucleic acid.

Alternatively, the first member of the binding pair may be an enzyme or enzyme substrate, and the complementary member is the corresponding enzyme substrate or enzyme, respectively. Alternatively, a substrate analog may be used in lieu of the enzyme substrate.

Other binding pairs useful in accordance with the present invention are disclosed in the other patents and patent applications discussed herein or will be apparent to those skilled in the art, and the use of such other binding pairs is specifically contemplated.

Therapeutic Agents

The first and second therapeutic agents may be the same or different, and may be, for example, therapeutic radionuclides, drugs, hormones, hormone antagonists, receptor antagonists, enzymes or proenzymes activated by another agent, autocrines or cytokines. Toxins also can be used in the methods of the present invention. Other therapeutic agents useful in the present invention include anti-DNA, anti-RNA, radiolabeled oligonucleotides, such as anti-sense oligodeoxy ribonucleotides, anti-protein and anti-chromatin cytotoxic or antimicrobial agents. Other therapeutic agents are described in the aforementioned U.S. patents and patent applications or are known to those skilled in the art, and the use of such other therapeutic agents in accordance with the present invention is specifically contemplated.

Isotopes, drugs, and toxins are preferred therapeutic agents. While the first and second therapeutic agents may be the same, in a preferred embodiment they are different. For example, the first and second therapeutic agents may comprise different radionuclides, or the first therapeutic agent may comprise a drug while the second therapeutic agent comprises a radionuclide, or the first therapeutic agent may comprise a radionuclide while the second therapeutic agent comprises a drug.

In a preferred embodiment, different isotopes which are effective over different distances as a result of their individual energy emissions are used as first and second therapeutic agents. This achieves more effective treatment of tumors, and is useful in patients presenting with multiple tumors of differing sizes, as in normal clinical circumstances.

As discussed above, few of the available isotopes are useful for treating the very smallest tumor deposits and single cells, and a drug or toxin may be a more useful therapeutic agent in these situations. Accordingly, in preferred embodiments of the present invention, isotopes are used in combination with non-isotopic species such as drugs, toxins, and neutron capture agents.

An isotope can be used in the first step, or in a subsequent step. Examples of suitable isotopes include P-32, P-33, Sc-47, Cu-64, Cu-67, As-77, Y-90, Rh-105, Pd-109, Ag-111, I-125, Pr-143, Sm-153, Tb-161, Ho-166, Lu-177, Re-186, Re-188, Re-189, Ir-194, Au-199, Pb-212 and Bi-213. When the isotope is used in the first step, it is preferred to use readily metabolizable isotopes, such as iodine. Examples of isotopes particularly useful in the first step of the present invention include I-125, I-131 and At-211. When the isotope is used in a subsequent step, it is preferred to use residualizing isotopes, such as yttrium-90.

Many drugs and toxins are known which have cytotoxic effects on cells, and can be used in connection with the present invention. They are to be found in compendia of drugs and toxins, such as the Merck Index, Goodman and Gilman, and the like, and in the references cited above. Examples of known cytotoxic agents useful in the present invention are listed, for example, in Goodman et al., "The Pharmacological Basis of Therapeutics," Sixth Edition, A. G. Gilman et al, eds./Macmillan Publishing Co. New York, 1980. These include taxol, nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocorticosteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used in the methods of the present invention; such drugs are known to these skilled in the art and include puromycin, cycloheximide, and ribonuclease.

Prodrugs are especially useful in the present invention as the inactive precursor of a therapeutic agent because the prodrug is relatively nontoxic in comparison to its active therapeutic metabolite. In the present invention, the prodrug can function as the second conjugate and the complementary member of a binding pair because it is the substrate for an enzyme which is the other member of the binding pair and is a component of the first conjugate. When the first conjugate is administered, it is targeted to the tumor by the targeting moiety. After the first conjugate is allowed sufficient time to localize and a clearing agent is optionally administered, then the prodrug; i.e., the second conjugate is administered. The prodrug binds to the enzyme component of the first conjugate at the tumor and is converted to the active metabolite which kills the tumor. Examples of such enzyme-prodrug binding partners are I-131-antibody-carboxypeptidase G2 and topoisomerase-inhibiting prodrug CPT-11; beta-lactamase and cephalosporin-doxorubicin; alkaline phosphatase and etoposide phosphate; carboxypeptidase G2 and glutamic acid derivative of benzoic acid mustard; and beta-glucuronidase and the glucuronide of any drug which can form a glucuronide, such as p-hydroxyaniline mustard. Other examples of targeted enzymes for prodrug activation are discussed in *Bioconjugate Chem.*, Vol. 4, (1), 3-9 (1993), and in U.S. patent application Ser. No. 07/182,623, which are herein incorporated in their entirety by reference.

The present invention also contemplates dyes used, for example, in photodynamic therapy, and used in conjunction with appropriate non-ionizing and ionizing radiation. Some isotopes, such as Y-90, emit an energy that can be used with photoactivating agents. The use of light and porphyrins in methods of the present invention is also contemplated and their use in cancer therapy has been reviewed. van den Bergh, *Chemistry in Britain*, 22: 430-437 (1986), which is incorporated herein in its entirety by reference.

As discussed above, toxins also can be used in the methods of the present invention. Toxins useful as therapeutics are known to those skilled in the art and include plant and bacterial toxins, such as, abrin, alpha toxin, diphtheria toxin, exotoxin, gelonin, pokeweed antiviral protein, ricin, and saporin. Toxins such as RNAases also may be used, for example, RNAse from frog oocytes, either recombinantly produced, may be used.

The other therapeutic agent may be delivered separately from the isotope. For example, a radioiodinated SAv-MAb conjugate may be administered to a patient, as described above. Then, optionally, a clearing agent of an anti-idiotypic MAb may be administered to remove residual circulating radioiodinated conjugate. Next, a biotinylated-polymer-drug conjugate or a biotin-toxin conjugate may be administered in a third step. This particular protocol is preferred for use in the therapy of smaller tumors, micrometastases and even single-cell dispersed, or minimal-cell, disease.

It is to be understood that any combination of the above described therapeutic agents may be used. For example, both the first and second therapeutic agents may be radioisotopes, the first therapeutic agent may be a radioisotope and the second therapeutic agent may be a drug, the first therapeutic agent may be a drug and the second therapeutic agent may be a radioisotope, the first therapeutic agent may be a radioisotope and the second therapeutic agent may be a toxin, the first therapeutic agent may be a toxin and the second therapeutic agent may be a radioisotope, both the first and second therapeutic agents may be drugs, or both the first and second therapeutic agents may be toxins.

While the above description teaches the use of two targeting species and two therapeutic agents, the present invention encompasses embodiments where more than two targeting species and/or therapeutic agents are used. For example, mixtures of radiometals which have different optimum ranges in tissue can be used with the same biotin-chelate in a single step. As a particular example, a mixture of the nuclides Y-90 (optimum tissue range 28-42 mm), praseodymium-143 (optimum tissue range 6-11 mm) and lutetium-177 (optimum tissue range 1.2-3.0 mm) can all be radiolabeled by the same biotin-chelate (comprising DTPA or macrocyclic DOTA derivatives, for instance) in the same reaction vessel to give biotin-chelate-complexes with comparable physico-chemical and biological clearance properties that comprise different isotopes. Making these conjugates is facilitated because most radioisotopes useful in radioimmunotherapy are available carrier-free, and many of those are heavy, tricationic metals like Y-90.

When a mixture of therapeutic agents is used, a plurality of therapeutic agents are delivered to the tumor sites, thereby enhancing the benefits of the method. The use of mixtures of nuclides has the further advantage that a greater percentage of the injected biotinylated chelates delivers a nuclidic payload to the tumor target.

Clearing Agents

Clearing agents known in the art may be used in accordance with the present invention. For example, if the first conjugate comprises avidin or streptavidin, biotin may be used as a clearing agent. Alternatively, if the first conjugate comprises biotin, avidin or streptavidin may be used as a clearing agent.

In a preferred embodiment, the clearing agent is an antibody which binds the binding site of the targeting species, where the targeting species can be an antibody, an antigen binding antibody fragment or a non-antibody targeting species. In a more preferred embodiment, the clearing agent is a MAb that is anti-idiotypic to the MAb of the conjugate used in the first step, as described in U.S. application Ser. No. 08/486,166. In another preferred embodiment, the clearing agent is substituted with multiple residues of carbohydrate, such as galactose, which allow the clearing agent to be cleared quickly from circulation by asialoglycoprotein receptors in the liver.

In a more preferred embodiment, the clearing agent is an anti-idiotypic MAb substituted with galactose and small numbers of biotin residues. Different purposes are being accomplished here. The anti-idiotypic MAb clears the first antibody conjugate (radioiodinated MAb-SAv) from circulation and deposits this into the hepatocytes. Because the anti-idiotypic MAb binds to the Mab binding region of the first antibody, it does not remove first antibody conjugate already localized at the tumor sites.

The multiple galactose substitution ensures the rapid clearance of the anti-idiotypic MAb into the liver hepatocytes, usually within minutes. Because the anti-idiotypic MAb is galactosylated and cleared rapidly, it does not have a chance to competitively remove the tumor-localized first antibody conjugate from the tumor over time. Also, there is very little myelotoxicity since almost all circulating radioactivity has been removed from the blood.

The small number of biotin residues on the anti-idiotypic MAb are sufficient to block that fraction of the streptavidin which is cleared into the liver, and remains for an extended period due to its inherent resistance to proteases.

From the above description, it will be evident that the invention can be used advantageously with the pre-targeting and amplification methods described in the above-cited U.S. patents and patent applications. For example, the first antibody conjugate may comprise a polymer to which are attached a plurality of streptavidin moieties, providing an increased number of binding sites for the subsequently administered biotin to bind, as described in U.S. Pat. No. 5,482,698.

The second conjugate of the present invention may comprise a naturally occurring metal-ion chelating protein capable of carrying a plurality of metal ions per protein to amplify the amount of metal ion therapeutic agent delivered to the tumor sites, as described in co-pending U.S. application Ser. No. 08/409,960, the contents of which are incorporated herein by reference in their entirety.

The present invention offers advantages over previous methods which deliver two therapeutic agents to a target site using a pre-targeting step followed by two delivery steps. For example, the method of the present invention has the advantage that each targeting composition has attached thereto a therapeutic agent. This is an advantage because each molecule delivered to the target site delivers a therapeutic agent to the target site, and therapy of the sites is amplified. Also, the present invention achieves delivery of a plurality of therapeutic agents in fewer steps than required by previous methods.

The use of the avidin/biotin binding pair in accordance with the present invention also offers amplification not necessarily achieved by other methods. For example, in the present invention, the avidin of the Ab-avidin-therapeutic agent conjugate has four binding sites available for binding subsequently administered biotin-therapeutic agent conjugates. In contrast, in other pre-targeting methods, one of the biotin-binding sites is used to target the avidin to the target site, for example, by binding to a biotin pre-targeted at the target site. This leaves only three biotin-binding sites available for binding the subsequently administered biotin conjugate. Thus, the present invention allows more biotin-therapeutic agent conjugate to be localized at the tumor sites.

EXAMPLES

The embodiments of the invention may be further illustrated through examples which show aspects of the invention in detail. These examples illustrate specific elements of the invention and are not to be construed as limiting the scope thereof.

Example 1

Targeted Double Therapeutic Agents

Preferred embodiments of targeted double therapeutic agents that can be delivered utilizing the method of the present invention include but are not limited to the following systems:

(1) I-131-antibody-biotin cleared (and tumor-avidinylated) with neutralized, deglycosylated avidin and targeted secondarily with Y-90-chelate-biotin.

(2) I-131-antibody-biotin cleared with an anti-idiotypic antibody, tumor-avidinylated with neutralized, deglycosylated avidin and targeted secondarily with Y-90-chelate-biotin.

(3) I-131-antibody-streptavidin cleared with an anti-idiotypic antibody and targeted secondarily with Y-90-chelate-biotin.

(4) I-131-antibody-streptavidin cleared with an anti-idiotypic antibody and targeted secondarily with Lu-177-chelate-biotin.

(5) I-131-antibody-streptavidin cleared with an anti-idiotypic antibody and targeted secondarily with camptothecin-biotin.

(6) I-131-antibody-streptavidin cleared with an anti-idiotypic antibody and targeted secondarily with onconase-biotin.

(7) I-131-antibody-streptavidin cleared with an anti-idiotypic antibody and targeted secondarily with pokeweed antiviral protein-biotin.

(8) I-131-antibody-streptavidin cleared with an anti-idiotypic antibody and targeted secondarily with endostatin-biotin.

(9) I-131-antibody-avidin (optionally neutralized and deglycosylated) cleared with an anti-idiotypic antibody and targeted secondarily with gelonin-biotin.

(10) I-131-bispecific antibody (such as anti-CEA and anti-Y-DOTA chelate) cleared with an anti-idiotypic antibody and targeted secondarily by a Y-90-DOTA derivative.

(11) I-131-bispecific antibody (such as anti-CEA and anti-doxorubicin) cleared with an anti-idiotypic antibody and targeted secondarily by a doxorubicin analog.

(12) I-131-bispecific antibody (such as anti-CEA and anti-ricin A chain) cleared with an anti-idiotypic antibody and targeted secondarily by a ricin A analog.

(13) I-131-biotinylated bispecific antibody (such as anti-CEA and anti-Y-DOTA chelate) cleared (and streptavidinylated at the tumor) with streptavidin and targeted secondarily by a Y-90-DOTA-biotin.

(14) I-131-antibody-avidin (optionally neutralized and deglycosylated) cleared with an anti-idiotypic antibody and targeted secondarily with I-125-antibody(3)-biotin.

(15) I-131-antibody-avidin (optionally neutralized and deglycosylated) cleared with an anti-idiotypic antibody and targeted secondarily with $(Y-90-DOTA)_8$-dextran-biotin.

(16) I-131-antibody-carboxypeptidase G2 cleared with an anti-idiotypic antibody and targeted secondarily with the topoisomerase-inhibiting prodrug CPT-11.

(17) I-131-antibody-avidin (optionally neutralized and deglycosylated) cleared with an anti-idiotypic antibody and targeted secondarily with ($^{10}$B-carborane)$_8$-dextran-biotin. The boron addend, targeted B-10, is then irradiated with thermal or epithermal neutrons to initiate neutron capture and generate cytotoxic alpha-particle and recoil nuclei. Examples of boron addends are described in copending U.S. patent application Ser. No. 08/687,626, which is herein incorporated by reference in its entirety.

In all of the above recited embodiments, there are little or no other non-target tissue binding sites available due to the clearance and metabolism of the first conjugate. In a preferred embodiment, the secondary recognition system utilized is foreign to the body being treated, thus minimizing non-specific binding and resulting in the attainment of a truer form of tumor specific targeting.

The therapeutic agents can be polymeric. In embodiment (11) above, doxorubicin analogs include the free drug, doxorubicin-dextran polymers and doxorubicin-PEG derivatives. PEG derivatives of second therapeutic agents are especially noteworthy because the serum residence time of such agents can be carefully controlled so that agents circulate for a sufficient period of time to saturate all pre-targeted tumor sites.

Embodiment 13 includes two recognition systems on the second conjugate; i.e., an antibody based and a biotin-streptavidin based recognition of the Y-90 therapy agent.

In embodiment (8), endostatin is an angiogenesis-inhibiting agent, similar to angiostatin.

Embodiments (5) and (11) are examples of employing commonly available anti-cancer drugs in the claimed methods, which is an advantage because these drugs can be administered in reduced amounts, and thus are less toxic, as compared to administering the free drug alone. Further, the receptor site for the drug is only present at the tumor, thus enhancing the tumor-to-tissue localization ratio. Generally, any standard chemotherapy drug can be used within the scope of the present invention but it is preferred that the major limiting toxicities of the two therapeutic agents be different. For example, myelosuppresssion is the major limiting toxicity of radioimmunotherapy, and it is not further increased by the use of bleomycin as the second therapy agent because its major limiting toxicity is pulmonary fibrosis.

Embodiment 14 as described in U.S. Pat. No. 5,525,338, herein incorporated in its entirety by reference, discloses the use of secondary targeted antibodies within pretargeting protocols. In this embodiment, the use of biotin-avidin recognition is supplemented by antibody(3) recognition of the same or a different epitope on the original target cell. In a similar manner, embodiment 15 as described in U.S. Pat. No. 5,482,698, herein incorporated in its entirety by reference, discloses many polymeric materials which enable amplification of targeting.

Embodiment 16 discloses a preferred embodiment which utilizes a prodrug within the scope of the present invention. Specifically, this embodiment uses the prodrug's relative lack of toxicity in comparison to its more active metabolite (i.e., SN-38), to further increase the difference between tumor and normal tissue toxicological effects.

Example 2

Targeting of a CEA-Producing Tumor with Two Different Radionuclides

Figure 2:
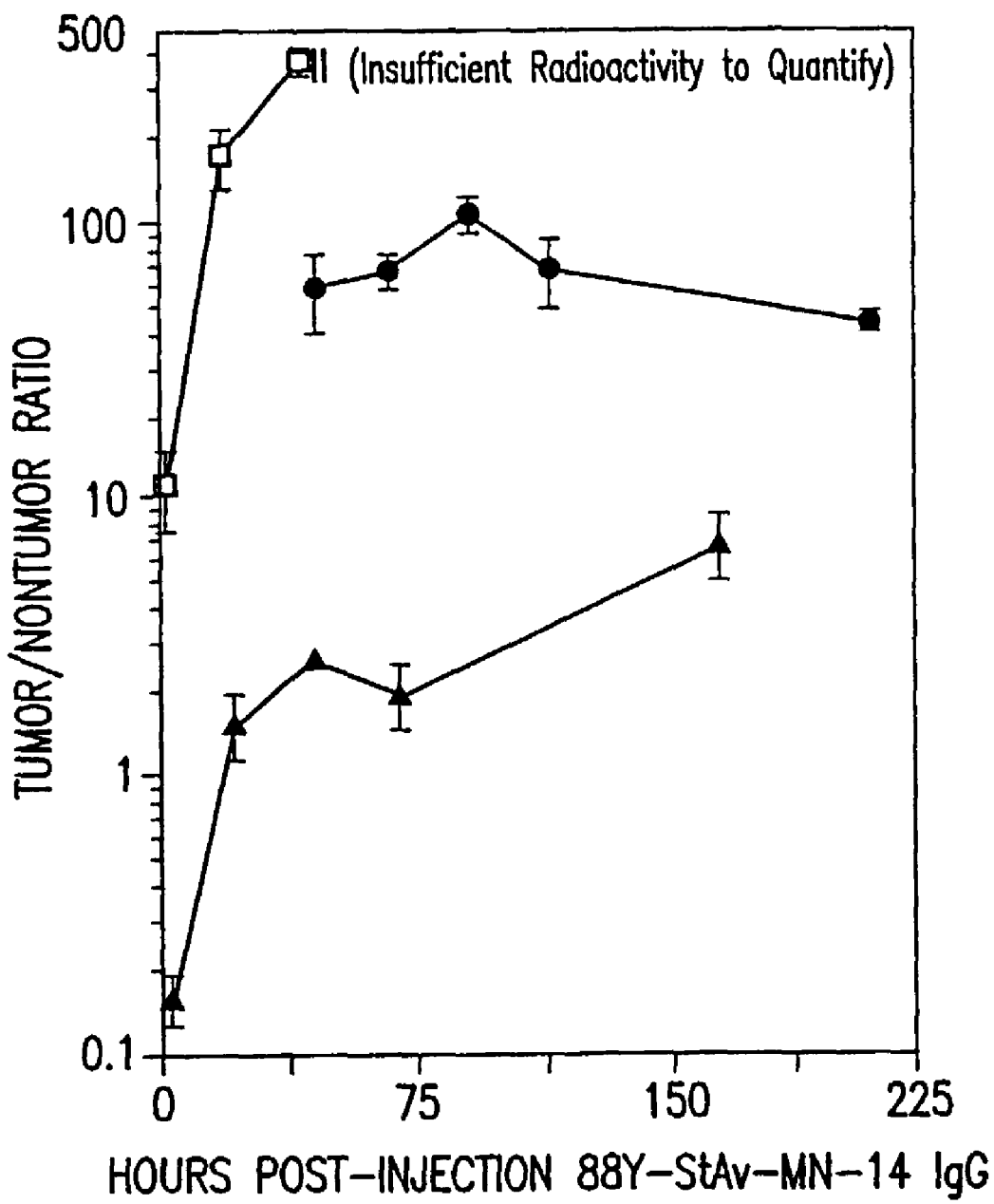
FIG. 2 shows the tumor-to-blood ratios for Y-88-DTPA-MN14 (anti-CEA)-streptavidin conjugate with and without clearing anti-idiotypic antibody to MN14, WI2; and 111-In-DTPA-pep-Biotin at continuing time points.

Nude mice bearing approximately one week old GW-39 (CEA-producing) human tumor xenografts are treated with an injection of a Y-88-DTPA-MN14 (anti-CEA)streptavidin radioimmunoconjugate. Forty-eight hours later the animals are treated with a five-fold molar excess (to remaining MN-14 in the circulation) of an anti-idiotypic antibody to MN14; WI2. Three hours later animals are injected with biotin-D-Phe-(epsilon-In-111-Bz-DTPA)-D-LysNH$_2$. After sacrifice and necropsy important tissues are counted separately in a gamma-scintillation counter using energy window settings appropriate for the two radionuclides; which, decaying at very different energies, can therefore be counted simultaneously. FIG. 1 shows the percentage ID/g of both agents in tumor at continuing time-points, while FIG. 2 shows the tumor-to-blood ratios for the reagents. It is found that tumor-to-blood ratios for the subsequently-administered biotin-D-Phe-(epsilon-In-111-Bz-DTPA)-D-LysNH$_2$ reach well over 100:1 within a very short time. Tumor-to-blood ratios of the Y-88-DTPA-MN14 also are around 80-100:1 at the time-points test. In comparison, Y-88-streptavidin-MN14 alone (as a model for standard radioimmunotherapy) only has a 2:1 tumor-to-blood ratio as late as 72 hours post-injection.

Example 3

Three-Step Radioimmunotherapy Delivering I-125 or I-131 and Y-90 to Tumor Sites

In this example a first antibody conjugate which comprises an anti-tumor MAb conjugated to streptavidin (SAv) and radiolabeled with an iodine isotope, such as I-131 or I-125, is administered to a patient.

After time of maximum tumor accretion, for example, about 24 to about 48 hours, a clearing composition comprising a conjugate of a MAb that is anti-idiotypic to the antibody of the first antibody conjugate is administered. This clearing agent clears first antibody conjugate from circulation.

The radioiodinated MAb-SAv localized at the tumor sites remains there, irradiating the tumor over very short ranges in the case of I-125 (single cell diameters) or over short to medium ranges in the case of I-131 (optimum range 0.26 to 0.5 cm). The radioiodinated MAb-SAv deposited internally in liver hepatocytes is metabolized and, the radioiodine is released and rapidly excreted from the patient.

Then, a conjugate is administered which comprises a biotinylated chelate carrying a radiometallic therapeutic nuclide; such as Y-90, as the second therapeutic agent. Because of the great affinity of biotin for streptavidin, the biotin-chelate-Y-90 conjugate rapidly binds to the tumor via the SAv moieties localized at the tumor site during the previous steps. Because the biotin-chelate-Y-90 conjugate is a low molecular weight species, non-localized conjugate is rapidly eliminated from the patient via the urine. Thus, a second therapeutic dose of radionuclide is delivered to the tumor site with minimal myelotoxicity.

Example 4

Three-Step Radioimmunotherapy Delivering I-131 and P-32 to Tumor Sites

This example takes advantage of the therapeutic effects of longer-lived nuclides and of the fact that nuclides localized at tumor sites in accordance with the present invention stay at the site for an extended period of time. This example also illustrates the use of a pair of complementary oligonucleotides as binding partners.

In the first step, a radioiodinated conjugate of a targeting MAb and a single-strand of an oligonucleotide, such as polyguanine, is administered. A galactosylated anti-idiotypic MAb is given at the time of maximum tumor localization to clear circulating first MAb conjugate, as discussed above. The second therapeutic isotope, P-32, is administered in the form of enzyme-resistant phosphorothioate esters bound to the single strand of an oligonucleotide that is complementary to the one used in the first step, in this case, polycytosine.

By this method, both I-131 and P-32 are delivered to the tumor sites.

Example 5

Therapy Delivering a Drug and Radioisotope to Tumor Sites

An SAv-MAb conjugate substituted with multiple drug moieties is administered to a patient. While a clearing agent step may be performed, it is optional. Because the initial conjugate is not carrying a radioactive isotope, omitting the clearing agent step should not have an adverse effect on the patient.

At the time of maximum tumor accretion a multi-biotinylated-polymer-lutetium-177 conjugate is given. That is, the conjugate comprises two or more biotin moieties. This latter conjugate binds to the SAv-MAb conjugate already localized at the tumor sites, cross-links the SAv-MAb conjugate and induces apoptosis and internalization. The tumor is then irradiated with the internalized, retained lutetium-177 radionuclide over an extended period, due to the nuclide's 7 day half-life. In another variation of this example, a mixture of "cocktail" of isotopes is used in the second step. Preferably, isotopes with different effective ranges are used.

Example 6

Combined Radioimmunotherapy and Toxin Immunotherapy Using a Three-Step Protocol

An iodine-131-labeled streptavidin-mAb conjugate is administered to a patient by injection. At the time of maximum tumor accretion of the conjugate, a circulatory clearing dose of a lightly biotinylated anti-idiotypic antibody is administered. This clearing agent removes non-targeted conjugate from the blood, and the I-131 is rapidly catabolized from the protein in the liver and is excreted. Conjugate targeted to the tumor sites remains at the tumor sites for an extended period of time, and irradiates the tumor cells. In the third step, the patient is injected with a toxin conjugate of (biotin)$_2$-onconase. The toxin localizes to the tumor sites via the pre-targeted streptavidin moieties. The doubly-biotinylated onconase is able to bind and cross-link the streptavidin-Mab conjugate, inducing internalization of the toxin into the tumor cells, which have already been irradiated with I-131, thereby effecting dual therapy of the tumor cells.

Example 7

Combined Radioimmunotherapy and Drug Immunotherapy Using a Three-Step Protocol

An iodine-131-labeled streptavidin-MAb conjugate is administered to a patient by injection. At the time of maximum tumor accretion of the conjugate, a circulatory clearing dose of a lightly biotinylated anti-idiotypic antibody is administered. This clearing agent removes non-targeted conjugate from the blood, and the I-131 is rapidly catabolized from the protein in the liver and is excreted. Conjugate targeted to the tumor sites remains at the tumor sites for an extended period of time, and irradiates the tumor cells.

In the third step, the patient is injected with a drug conjugate of (biotin)$_2$-dextran-(doxorubicin)$_{10}$. The drug localizes to the tumor sites via the pre-targeted streptavidin moieties. The doubly-biotinylated polymeric drug is able to bind and cross-link the streptavidin-Mab conjugate, inducing internalization of the doxorubicin into the tumor cells, which have already been irradiated with I-131, thereby effecting dual therapy of the tumor cells.

Example 8

Preparation of Poly-∀-Glutamic Acid (SN-38-(-Ester)$_{10}$

A 10 g ($2-6.66 \times 10^{-4}$ mole) amount of poly-∀-glutamic acid (15-50 kdalton; Sigma Chemical Company) is mixed with 200 mL of dry, distilled dimethylformamide (DMF) and 3.92 g ($1 \times 10^{-2}$ mole) SN-38. By means of a hydrogen chloride generator system (slow mixing of hydrochloric and concentrated sulfuric acid and passage of the resulting gas through concentrated sulfuric acid) dry hydrogen chloride gas is added to the DMF until a weight increase of 5 g has occurred. The mixture is heated under reflux for three hours using a Soxhlet extractor filled with dry magnesium sulfate to remove water from the DMF prior to its return to the reaction vial. After cooling, the product, poly-∀-glutamic acid (SN-38-(-ester)$_{10}$, in DMF is treated with a ten-fold excess of diethyl ether to DMF. The collected precipitate is washed with ether, taken up in water and the aqueous solution extracted with chloroform to remove residual free SN-38. Poly-∀-glutamic acid (SN-38-(ester)$_{10}$ is collected as a lyophilized solid and the SN-38-to-polymer ratio determined spectrophotometrically.

Example 9

Preparation of AcLys(DTPA)Glu$_6$[SN-38]$_6$Lys [DTPA]NH$_2$

The title peptide is prepared as a discrete entity using standard solid-phase synthetic methods with the first resin-appended lysine residue substituted with an allyloxycarbonyl (aloc) epsilon protecting group and the last [N-terminus] lysyl residue protected similarly at its epsilon amino position. The N-terminus is acetylated at the conclusion of the chain synthesis. The glutamic acid gamma carboxyl groups are protected as the tert.-butyl esters during peptide assembly. Alpha amino groups are protected using Fmoc and the peptide is prepared on solid phase with successive rounds of Fmoc deprotection and coupling. Then, the two-epsilon aloc groups are selectively removed. The partially protected peptide is reacted with an excess of tetra-tert-butyl DTPA through its free carboxyl group. Finally, the tert-butyl protecting groups are removed from the lysyl and DTPA carboxyl residues, respectively, and the peptide cleaved from the resin, with trifluoroacetic acid. The released intermediate is ready for reaction with a suitably activated drug. SN-38 and the above peptide are reacted together in toluene using acid catalysis and Dean-Stark conditions to produce AcLys(DTPA)Glu$_6$[SN-38]$_6$Lys[DTPA]NH$_2$ with the SN-38 linked to the peptide glutamate gamma carboxyl groups as esters.

Example 10

Dual Therapy Using a Radiolabeled Bispecific Antibody and a Drug-Polymer Conjugate A patient with a CEA=–expressing tumor is treated with an I-131-labeled anti-CEA×anti-camptothecin bispecific antibody, which is allowed to target CEA-expressing tumor cells, and substantially clear circulation and normal tissues. When this has happened the patient is further treated with the conjugate poly-∀-glutamic acid (SN-38-(-ester)$_{10}$.

It will be apparent to those skilled in the art that various modifications and variations can be made to the processes and compositions of this invention. Thus, it is. intended that the present invention cover the modifications and variations of this invention provided they come within the scope of the appended claims and their equivalents.

What is claimed is:

1. A method for treating a patient with cancer comprising:
    (A) delivering a first conjugate comprising a multispecific antibody or antibody fragment and a first anti-cancer agent, wherein said multispecific antibody or antibody fragment binds to
        (i) at least one marker substance selected from the group consisting of carcinoembryonic antigen (CEA), epidermal growth factor receptor (EGFR), CD20, colon-specific antigen-p (CSAp), HLA-DR, human chorionic gonadrotropin, prostatic acid phosphatase (PAP), mammary tumor-associated glycoprotein, ovarian cystadenocarcinoma-associated antigen, ovarian tumor specific antigen, cervical cancer antigen, cytoplasmic melanoma associated antigen, melanoma cell surface antigen, breast cancer cell surface antigen, lung cancer cell surface antigen, colorectal cancer cell surface antigen, gastric cancer cell surface antigen, pancreatic cancer cell surface antigen, glioma cell surface antigen, common sarcomal cell surface antigen, gastrointestinal cancer cell surface antigen, brain tumor cell surface antigen, esophageal cancer cell surface antigen, common epithelial cancer cell surface antigen, osteosarcoma cell surface antigen, fibrosarcoma cell surface antigen, urinary bladder cancer cell surface antigen, prostatic cancer cell surface antigen, renal cancer cell surface antigen, ovarian cancer cell surface antigen, testicular cancer cell surface antigen, endometrial cancer cell surface antigen, Hodgkin's disease cell surface antigen, lymphoma cell surface antigen, leukemic cell surface antigen and trophoblastic tumor cell surface antigen, said cancer selected from the group consisting of a carcinoma, sarcoma, glioma, lymphoma, leukemia, melanoma and myeloma; and
        (ii) a first hapten;
    (B) optionally, administering a clearing agent;
    (C) delivering a second conjugate comprising a second hapten wherein said second hapten crosslinks to more than one multispecific antibodies or antibody fragments to increase cellular internalization, and a second anti-cancer agent, wherein said second anti-cancer agent comprises a drug-polymer conjugate; and
    (D) inducing said cellular internalization of said multispecific antibody or antibody fragment.

2. The method of claim 1, wherein said multispecific antibody or antibody fragment binds to a first marker as recited in claim 1 and a second marker as recited in claim 1, wherein said second marker is different from said first marker.

3. The method of claim 1, wherein said multispecific antibody or antibody fragment binds to a first epitope and a second epitope on a marker as recited in claim 1, wherein said first epitope is different from said second epitope.

4. The method of claim 1, wherein said multispecific antibody or antibody fragment is a chimeric multispecific antibody or antibody fragment.

5. The method of claim 1, wherein said multispecific antibody or antibody fragment is a humanized multispecific antibody or antibody fragment.

6. The method of claim 1, wherein said multispecific antibody or antibody fragment is a fusion protein.

7. The method of claim 6, wherein said fusion protein is a bispecific fusion protein.

8. The method of claim 7, wherein said bispecific fusion protein comprises a scFv fragment and a Fab fragment, wherein said scFv fragment comprises one binding site for a first marker substance and said Fab fragment comprises one binding site for a second marker substance.

9. The method of claim 7, wherein said bispecific fusion protein comprises an IgG and two scFv fragments, wherein said IgG comprises two binding sites for a first marker substance, and said two scFv fragments comprises two binding sites for a second marker substance.

10. The method of claim 1, wherein each conjugate is generated by recombinant technology.

11. The method of claim 1, wherein the second conjugate comprises HSG (histamine-succinyl-glycine).

* * * * *